United States Patent [19]
Gogolewski et al.

[11] Patent Number: 5,236,431
[45] Date of Patent: Aug. 17, 1993

[54] RESORBABLE FIXATION DEVICE WITH CONTROLLED STIFFNESS FOR TREATING BODILY MATERIAL IN VIVO AND INTRODUCER THEREFOR

[75] Inventors: Sylwester Gogolewski, Alvaneu; Stephan M. Perren, Davos, both of Switzerland

[73] Assignee: Synthes, Paoli, Pa.

[21] Appl. No.: 733,598

[22] Filed: Jul. 22, 1991

[51] Int. Cl.⁵ .................................. A61B 17/56
[52] U.S. Cl. ................................ 606/72; 606/77
[58] Field of Search .............. 606/72, 73, 74, 75, 606/77, 86, 90, 99, 103, 104, 220, 230; 411/456, 508, 509, 510, 913

[56] References Cited

U.S. PATENT DOCUMENTS

| | | | |
|---|---|---|---|
| 3,029,486 | 4/1962 | Raymond | 411/509 |
| 3,272,059 | 9/1966 | Lyday | 411/510 |
| 3,309,955 | 3/1967 | Turnbull | 411/509 |
| 3,350,976 | 11/1967 | Topf | 411/510 |
| 3,860,999 | 1/1975 | Meyer | 411/510 |
| 4,233,878 | 11/1980 | McGauran | 411/510 |
| 4,392,278 | 7/1983 | Mugglestone | 411/510 |
| 4,924,865 | 5/1990 | Bays | 606/77 |
| 4,976,715 | 12/1990 | Bays | 411/510 |

FOREIGN PATENT DOCUMENTS 1163572 9/1969 United Kingdom ............ 411/509

Primary Examiner—Robert A. Hafer
Assistant Examiner—Michael Brown
Attorney, Agent, or Firm—McAulay, Fisher, Nissen, Goldberg & Kiel

[57] ABSTRACT

The resorbable fixation device is useful for treating torn bodily material in vivo. It has a tip, a head, and a cylindrically shaped shaft portion lying between the tip and the head. The shaft portion has at least one retention element protruding radially therefrom to facilitate insertion of said shaft portion longitudinally into the bodily material in a forward axial direction extending from the tip to the head and to restrict movement of the shaft portion through the bodily material in a backward axial direction opposite to the forward direction. The shaft portion has further a hollow body with at least one radial opening extending transversely through the walls surrounding the hollow body and rendering the shaft radially elastic. The walls surrounding the hollow body are provided with at least one stiffening element providing a controlled stiffness to the fixation device.

21 Claims, 7 Drawing Sheets

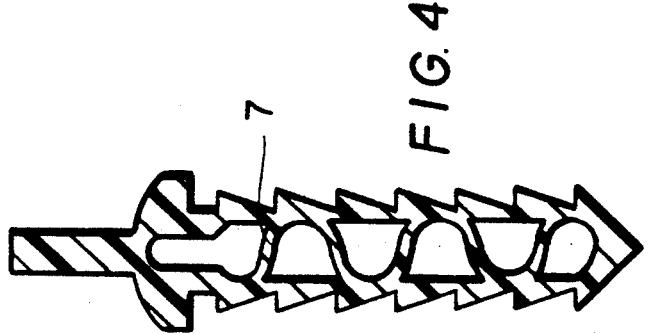 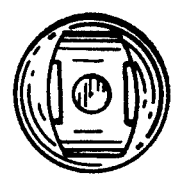
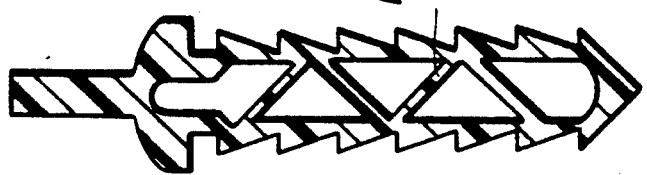 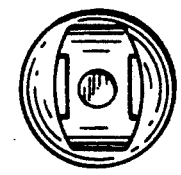
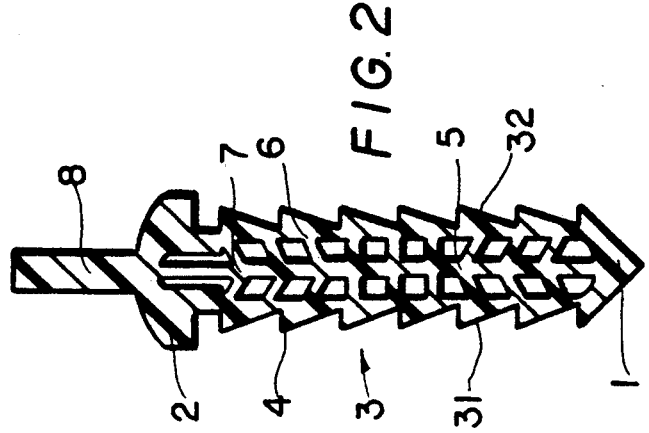 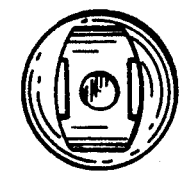

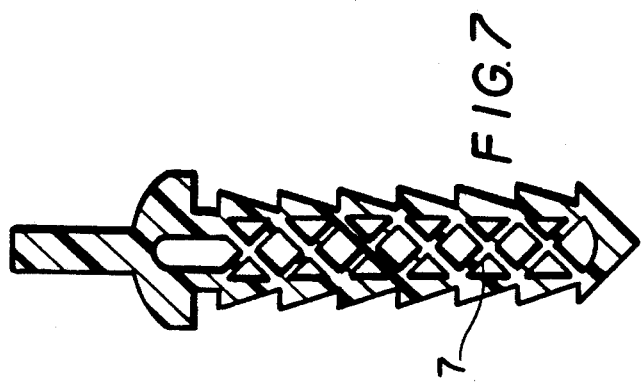
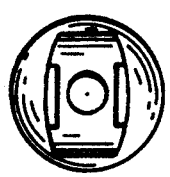
FIG.7
FIG.7A
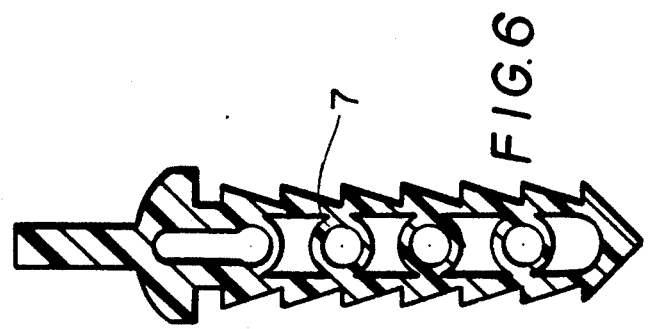
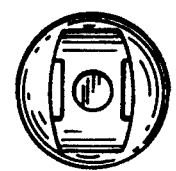
FIG.6
FIG.6A
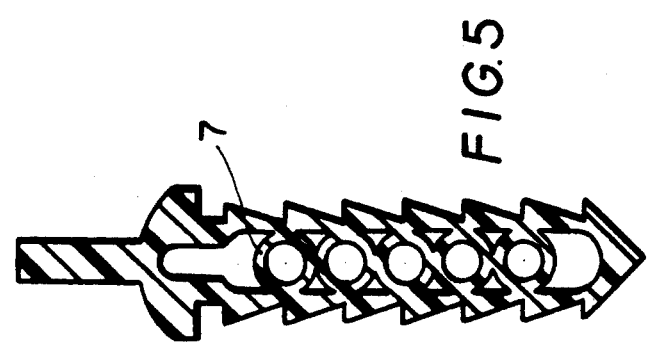
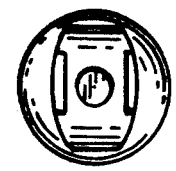
FIG.5
FIG.5A

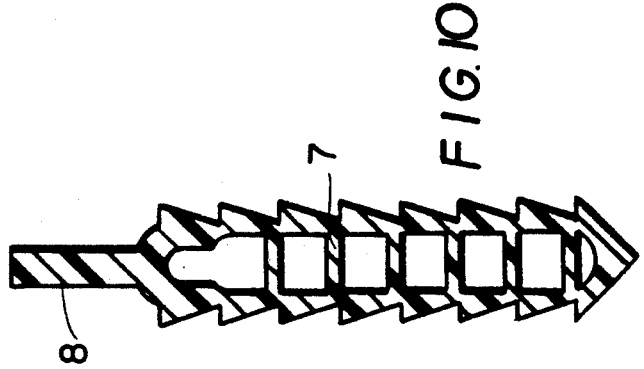
FIG.10    FIG.10A
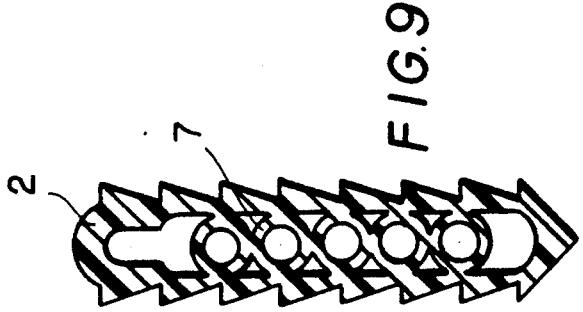
FIG.9    FIG.9A
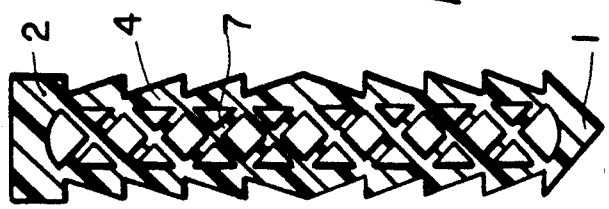
FIG.8    FIG.8A

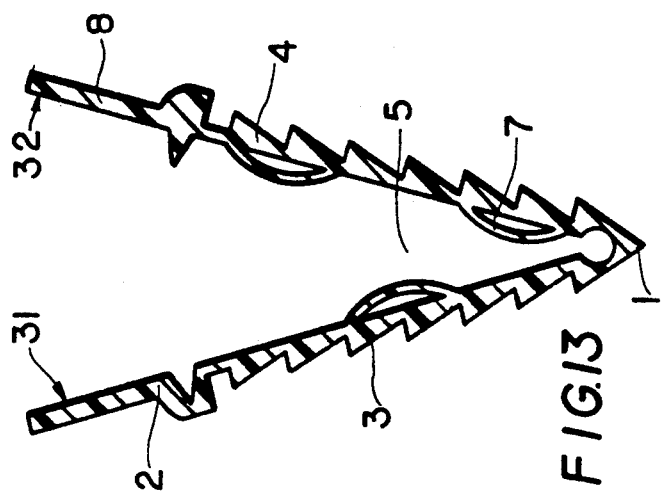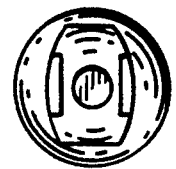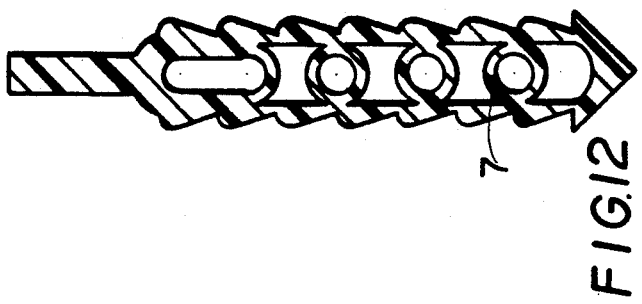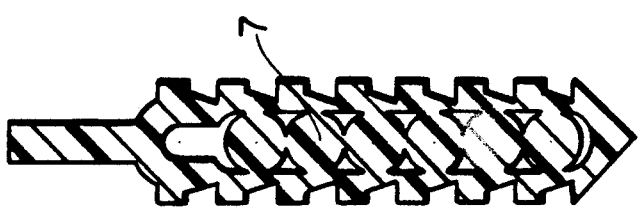

RESORBABLE FIXATION DEVICE WITH CONTROLLED STIFFNESS FOR TREATING BODILY MATERIAL IN VIVO AND INTRODUCER THEREFOR

BACKGROUND OF THE INVENTION a) Field of the Invention

This invention relates to a resorbable fixation device for treating torn bodily material in vivo.

b) Background Art

Internal fixation of facial bones is usually performed using various types of metallic dynamic compression plates, miniplates and adequate screws. Although metallic implants give satisfactory fixation and good fracture healing, it is recommended to remove them after the fracture healing is completed. This is basically due to potential corrosion of the implants, bone resorption under the implant and possible inflammatory response to the implant. The use of resorbable implants with adequate mechanical properties and rate of resorption might allow to overcome these problems.

Traumatic injury and/or heavy load applied to the knee may result in torn menisci. The early methods of treatment of the torn menisci involved partial or total meniscectomy. The long term results of the latter technique proved to be disappointing, and often led to osteoarthritis and instability of the knee. The new techniques of menisci lesions repair involve meniscus suturing using arthrotomy and arthroscopy. An arthrotomy is quite traumatic, as it requires large incision to gain access to the joint. An arthroscopy allowing guiding the suture under arthroscopic visualization is less traumatic, although it also requires incision which is larger than the standard one used in arthroscopy.

From U.S. Pat. No. 4,884,572 BAYS ET AL. a fixation device is known for repairing torn cartilaginous or other bodily tissue, particularly torn meniscus tissue during arthroscopic surgery. This known repair device in the form of a tack has a shaft portion with radially projecting barb members and a longitudinal bore. It is made from a biodegradable material chosen to have a degradation time in excess of the required healing time for the tissue, i.e. glycolide and lactide copolymers. This known device of conventional design seems to improve the torn meniscus treatment technique because it requires only a small incision. It is not possible, however, to use it for treatment of small fragments due to its lack of sufficient stiffness.

It is further known to use resorbable pins (marketed under the trademarks ORTHOSORB, ETHIPIN and BIOFIX) for the fixation of small fragments, treatment of fractures of the ankle, talus, patella, condylar fractures of the femur, fractures of the metacarpals and phalanges of the hand, condylar fractures of the humerus, a.s.o. These known pins have a circular cross-section and a smooth surface. The latter may give rise to pin loosening due to the slippage of the smooth surface through the bone hole. In addition, in their present design and sizes, they are available only with one stiffness.

SUMMARY OF THE INVENTION

The invention as claimed is intended to remedy these drawbacks. It solves the problem of how to design a resorbable fixation device with a controlled stiffness for treating torn bodily material in vivo.

The invention solves the problem with a resorbable fixation.

The resorbable fixation device for treating torn bodily material in vivo has a trip, a head, and a cylindrically shaped shaft portion lying between the tip and the head. The shaft portion has at least one retention element protruding radially therefrom to facilitate insertion of the shaft portion longitudinally into the bodily material in a forward axial direction extending from the tip to the head and to restrict movement of the shaft portion through the bodily material in a backward axial direction opposite to the forward direction. The shaft portion has a hollow body with at least one radial opening extending transversely through the walls surround the hollow body and rendering the shaft radially elastic. The walls are provided with at least one stiffening element.

The introducer is for implanting a resorbable fixation device of elongated cylindrical shape with a grip portion. The introducer comprises a threaded pusher engaging with the upper portion of a threaded hollow cylindrical member having longitudinal cuttings in the lower conical part and a load transmitting ball which, by screwing forward, the pusher presses the lower conical part of the hollow cylindrical member and opens the jaws for receiving the grip portion of the fixation device and, by screwing backward, the pusher is pushed backward by the opened jaws, the latter clamping releasably the grip portion of the fixation device.

In a preferred embodiment of the fixation device according to the invention its stiffening elements are arranged along the inner side of the walls surrounding its hollow body and protrude therein. The number and geometrical shape of the stiffening elements can be varied over a great range. The resulting overall stiffness of the fixation device can be varied, by varying the number of stiffening elements and their shape, and this can be adjusted to a particular application.

For fixation devices with stiffening elements of the same thickness or diameter, increasing the number of stiffening elements being located within the hollow body, i.e. decreasing the distance between the individual elements, increases the overall stiffness of the respective device.

Fixation devices having stiffening elements with rectangular shape, or solid cross-sections have higher stiffness, than those having X-type, S-type and D-type shapes and hollow cross-sections.

In a further preferred embodiment of the invention the head of the fixation device is divided by the radial opening or slit through the shaft thereby allowing lateral movement of the two lateral segments formed by the slit and rendering the device expandable.

The use of the hollow body which has a radial opening or slit reduces the amount of polymer necessary for producing the implant, and thus diminishes the chance of the long -term tissue inflammation. Furthermore resorbability of the polymer material which through the opening is accessible from all sides to the bodily fluids is enhanced.

The shape of the retention elements ca be varied to achieve best contact between the tissue and the implant and thus, fixation stability. In a further preferred embodiment of the invention the orientation of the retention elements in the upper shaft portion adjacent to the head is reversed in the opposite direction. This design enhances fixation stability of the tissue and allows compression of the fracture fragments.

The fixation device according to the invention can be used with a grip portion attached to the head or without, depending on the area of application. The grip portion allows controlled handling and inserting of the fixation device into bodily tissues with the aid of a hollow introducer allowing a releasable engagement with the fixation device. The grip portion is preferably provided with a predetermined breaking point and is finally cut or broken out, once the device is introduced in the tissue.

The various features of novelty which characterize the invention are pointed out with particularity in the claims annexed to and forming part of this disclosure. For the better understanding of the invention, its operating advantages and specific objects attained by its use, reference should be had to the accompanying drawings and descriptive matter in which are illustrated and described preferred embodiments of the invention.

BRIEF DESCRIPTION OF THE DRAWINGS

In the drawings:

FIGS. 2 to 12 show longitudinal sections and cross-sectional views of various fixation devices according to the invention having various arrangements of stiffening elements and retention elements;

FIG. 13 shows a longitudinal section of a fixation device according to the invention with a split head portion and expandable shaft segments;

DESCRIPTION OF THE PREFERRED EMBODIMENTS

Figure 1:
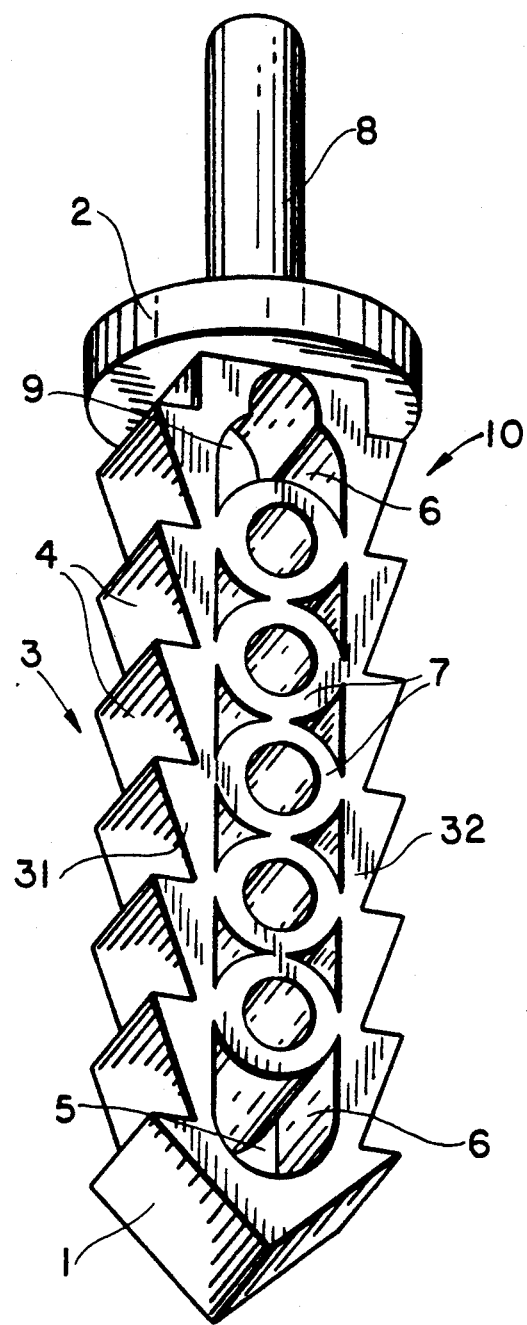
FIG. 1 shows a perspective view of a fixation device according to the invention.

A shown in FIG. 1, the fixation device according to the invention basically consists of an elongated cylindrical body 10 with a tip 1, a head 2, and a cylindrically shaped hollow shaft portion 3 lying between said tip 1 and said head 2. The shaft portion 3 is rectangular in cross-section, but could also be circular. The length of the shaft 3 is predetermined and depends from the area of application. The shaft portion 3 has a plurality of retention elements 4 protruding radially therefrom to facilitate insertion of said shaft portion 3 longitudinally into said torn bodily material in a forward axial direction extending from said tip 1 to said head 2 and to restrict movement of said shaft portion 3 through said bodily material in a backward axial direction opposite to said forward direction. The shaft portion 3 contains a hollow body 9 with a radial opening 5 in the form of a longitudinal slit extending transversely through the walls 6 surrounding said hollow body 9. This construction of the shaft 3 with the radial opening 5 which divides it into two lateral segments 31 and 32—connected at the tip 1 and at the head 2—provides it with radial elasticity.

Along the inner side of said walls 6 surrounding said hollow body 9 a number of stiffening elements 7, in the form of hollow tube segments, are arranged and protrude into the hollow body 9. The stiffening elements 7 are arranged in a regular pattern along the axial direction of the shaft portion 3 and are connecting the two lateral segments 31 and 32 providing a controlled stiffness of the shaft portion 3.

The stiffening elements 7 can have various shapes as illustrated in FIGS. 1 to 12. Instead of the hollow tube segments—as illustrated in FIGS. 1, 5 6, 9 and 12—a multitude of other stiffening elements are suitable, e.g. with rectangular shape (FIG. 10), solid cross-sections (FIG. 11), X-type structure (FIG. 7 and 8), Z-type structure (FIG. 3), S-type structure (FIG. 4) or lattice structure ((FIGS. 2).

All embodiments according to FIGS. 1 to 12 have an integral head 2 which preferably is provided with a grip portion 8 (FIGS. 1 to 8 and 10 to 12). The grip portion is designed for releasable engagement by a hollow introducer as explained below, said grip portion 8 being preferably provided with a predetermined breaking or cutting point.

In FIG. 13 a preferred embodiment of a fixation device is illustrated with a head 2 which is also divided by said radial opening 5 in the form of a longitudinal slit allowing lateral movement of said two lateral segments 31 and 32 around said tip 1 which connects them.

In a preferred embodiment illustrated in FIG. 8 the orientation of the retention elements 4 in the upper shaft portion 3 adjacent to said head 2 is reversed in the opposite direction adjacent to the tip 1.

Figure 15:
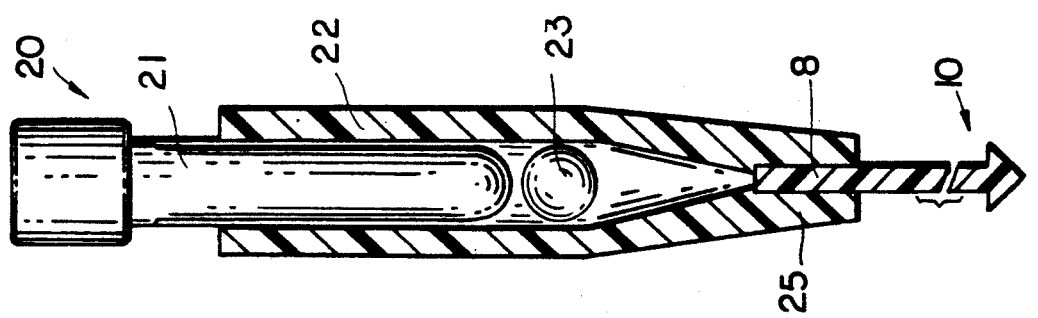
FIG. 15 shows a longitudinal section of the introducer according to FIG. 14.
Figure 14:
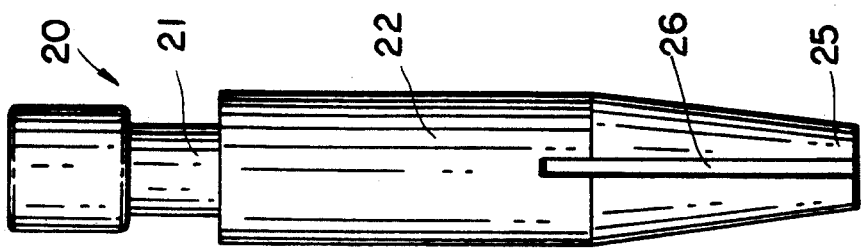
FIG. 14 shows a side view of a screw-actuated introducer to be used for inserting the fixation devices according to the invention.
Figure 14A:
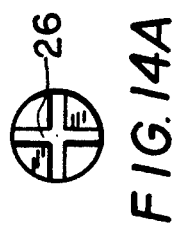

The screw-activated introducer 20 shown in FIGS. 14 and 15 consists of a threaded pusher 21 engaging with the upper portion of a threaded hollow cylindrical member 22 having longitudinal cuttings 26 in the lower conical part and a load transmitting ball 23. By screwing in the pusher 21, it pushes the load transmitting ball 23 in the forward direction, which in turn pushes the lower conical part of the hollow cylindrical member 22 and opens the jaws 25 for receiving the grip portion 8 of the fixation device 10. By screwing out the pusher 21, the load transmitting ball 23 is pushed backward by the opened jaws 25, the latter clamping releasably the grip portion 8 of the fixation device 10 as represented in FIG. 15. Next the fixation device 10 can be implanted in the tissue and the grip portion 8 can be cut out.

Figure 16:
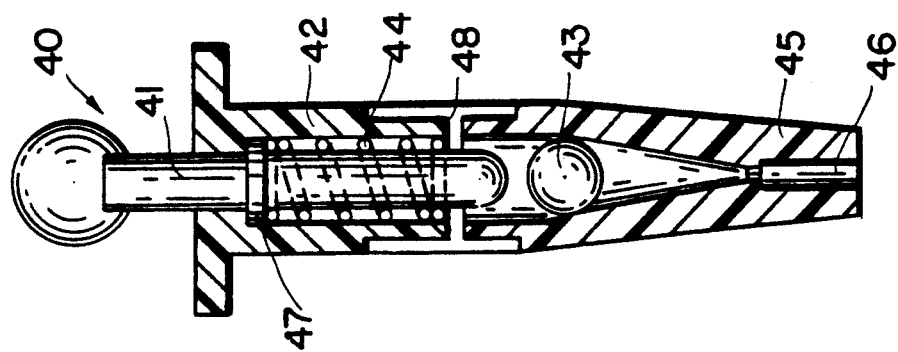
FIG. 16 shows a longitudinal section of a spring-actuated introducer to be used for inserting the fixation devices according to the invention with a grip portion.

The spring-activated introducer 40 shown in FIG. 16 consists of a spring-activated pusher 41 with an annular stop 47 for a spring 44 engaging with the upper portion of a hollow cylindrical member 42 with an annular stop 48 for the spring 44 and having longitudinal cuttings 46 in the lower conical part, and a load transmitting ball 43. It uses the same principle as the screw-activated introducer 20 except that opening and closing of the jaws 45 of the introducer 40 are activated by the spring 44, and under action of the spring 44, the pusher 41 returns to its dwelling position.

Figure 18:
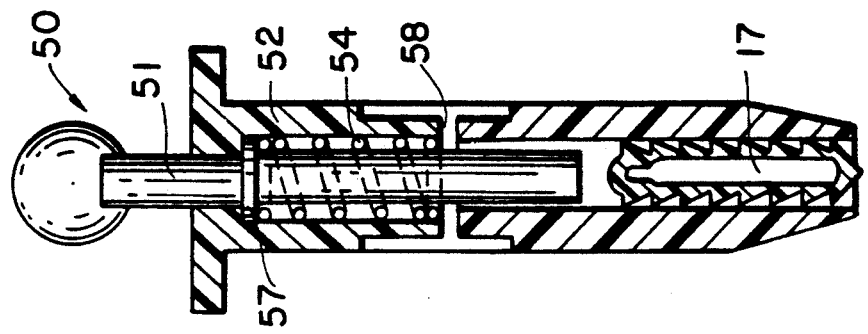
FIG. 18 shows a cross-section of the introducer according to FIG. 17.
Figure 17:
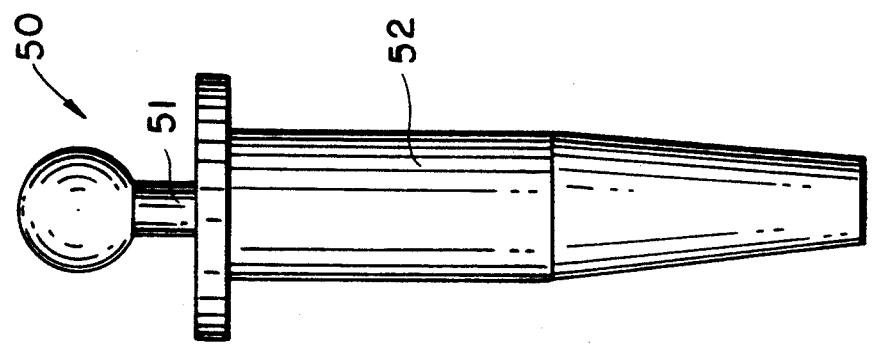
FIG. 17 shows a side-view of a spring-actuated introducer to be used for inserting the fixation devices according to the invention without a grip portion.

The spring-activated introducer 50 shown in FIGS. 17 and 18 consists of a spring-activated pusher 51 with an annular stop 57 for a spring 54 engaging with the upper portion of an unslitted hollow cylindrical member 52 with an annular stop 58 for the spring 54 and with a cylindrical implant chamber 57 adapted to receive a fixation device 17 which does not have a grip portion attached to the head 2.

The introducers 20, 40 and 50 allow good handling and easy implantation of the fixation devices according to the invention.

Resorbable materials to be used for preparing of the fixation devices according to the invention are mainly polymers such as highly purified polyhydroxyacids, polyamines, polyaminoacids, copolymers of amino acids and glutamic acid, polyorthoesters, polyanhydrides, polyamides, polydioxanone, polydioxanediones, polyesteramides, polymalic acid, polyesters of diols and oxalic and/or succinic acids, polycaprolactone, copolyoxalates, polycarbonates or poly(glutamic-co-leucine). Preferably used polyhydroxyacids comprise polycaprolactone, poly(L-lactide), poly(D-lactide), poly(L/D-lactide), poly(L/DL-lactide) polyglycolide, copolymers of lactide and glycolide of various compositions, copolymers of said lactides and/or glycolide with other polyesters, copolymers of glycolide and trimethylene carbonate, poly(glycolide-co-trimethylene carbonate), polyhydroxybutyrate, polyhydroxyvalerate, copolymers of hydroxybutyrate and hydroxyvalerate of various compositions.

Further materials to be used as additives are composite systems containing resorbable polymeric matrix and resorbable glasses and ceramics based e.g. on tricalcium phosphate and/or hydroxyapatite, admixed to the polymer before processing.

The rate of resorption and the loss of mechanical properties of the fixation device according to the invention in vivo has to be adapted to allow maintenance of its functionality during the healing period. The rate of resorption can be controlled taking into account that such factors as polymer weight, crystallinity, polymer chain orientation, material purity, the presence of copolymer unit in the chain and presence of voids (porosity) will affect the rate of resorption. In general the rate of resorption increases in the presence of a material with voids, pores, impurities, copolymer units. The rate of degradation decreases with the increase of polymer molecular weight, crystallinity and chain orientation. The polymeric material should preferably have a degradation rate in vivo in the range of 6 weeks to 24 months. Viscosity-average molecular weight of polymers to be suitable for preparation of the fixation device according to the invention should be in the range of 30.000 to 900.000 and preferably 150.000 for soft tissue implants, and preferably 300.000 to 400.000 for hard tissue implants.

Concentration of the copolymer unit in the polymer should be in the range of 1 to 99% and preferably in the range of 5 to 35%.

The polymeric material should preferably have a polydispersity in the range of 1.2 to 100.0, most preferably in the range of 1.5 to 3.0.

The flexural strength of the fixation devices according to the invention should exceed 60 MPa, preferably 100 MPa. Its modulus of elasticity should exceed 7 MPa, preferably 10 MPa.

The resorbable or degradable polymeric and/or polymeric-ceramic materials to be used for the fixation device according to the invention should have a Young's modulus in the range of 1 to 50 GPa and a tensile strength in the range of 0.1 to 20.0 GPa. The Young's modulus should preferably be in the range of 5 to 15 GPa, most preferably in the range of 7 to 10 GPa. The tensile strength should preferably be in the range of 0.5 to 3.0 GPa, most preferably in the range of 0.7 to 2.5 GPa.

The polymeric material should preferably have a at least partially oriented structure. Resorbable fixation devices according to the invention can be produced using standard techniques of polymer processing, mainly by injection-moulding, compression-moulding and in-mould polymerization.

Typical absolute dimensions of the fixation device according to the invention, e.g. for maxillofacial surgery are:
length 6 to 8 mm;
diameter 1.8 to 2.5 mm.

Dimensions of fixation devices for treatment of small fragments and/or osteochondral defects are:
length 20 to 40 mm;
diameter 1.5 to 4 mm.

While the foregoing description and drawings represent the preferred embodiments of the present invention, it will be obvious to those skilled in the art that various changes and modifications may be made therein without departing from the true spirit and scope of the present invention.

We claim:

1. In a resorbable fixation device for treating torn bodily material in vivo having a tip, a head, and a cylindrically shaped shaft portion lying between said tip and said head, said shaft portion having at least one retention element protruding radially therefrom to facilitate insertion of said shaft portion longitudinally into said bodily material in a forward axial direction extending from said tip to said head and to restrict movement of said shaft portion through said bodily material in a backward axial direction opposite to said forward direction, the improvement comprising that said shaft portion has internal walls defining a longitudinal hollow portion with at least one radial opening extending transverse thereto and rendering said shaft portion radially elastic;

said shaft portion being provided with at least one stiffening element arranged along the inner side of said walls and protruding into said hollow portion; and said radial opening being in the form of a longitudinal slit dividing said shaft into two lateral segments connected at least at said tip.

2. Device according to claim 1, wherein a plurality of said stiffening elements is arranged in said axial direction, preferably in a regular pattern.

3. Device according to claim 1, wherein said stiffening elements are connecting said two lateral segments.

4. Device according to claim 1, wherein said head is also divided by said radial opening in the form of a longitudinal slit allowing lateral movement of said two lateral segments around said tip which connects them.

5. Device according to claim 1, wherein its flexural strength exceeds 60 MPa.

6. Device according to claim 5, wherein its flexural strength exceeds 100 MPa.

7. Device according to claim 1, wherein its modulus of elasticity exceeds 7 MPa.

8. Device according to claim 7, wherein its modulus of elasticity exceeds 10 MPa.

9. Device according to claim 1, wherein it comprises resorbable or degradable polymeric and/or polymeric-ceramic material, having
a Young's modulus in the range of 1 to 50 GPa; and
a tensile strength in the range of 0.1 to 20.0 GPa.

10. Device according to claim 9, wherein said Young's modulus is in the range of 5 to 15 GPa, preferably in the range of 7 to 10 GPa.

11. Device according to claim 9, wherein said tensile strength is in the range of 0.5 to 3.0 GPa, preferably in the range of 0.7 to 2.5 GPa.

12. Device according to claim 9, wherein at least 90 weight percent of said polymeric material has a molecular weight in the range of 100,000 to 900,000.

13. Device according to claim 12, wherein at least 90 weight percent of said polymeric material has a molecular weight in the range of 200,000 to 350,000.

14. Device according to claim 9, wherein said polymeric material comprises highly purified polyhydroxyacids, polyamines, polyaminoacids, copolymers of amino acids and glutamic acid, polyorthoesters, polyanhydrides, polyamides, polydioxanone, polydioxanediones, polyesteramides, polymalic acid, polyesters of diols and oxalic and/or succinic acids, polycaprolactone, copolyoxalates, polycarbonates or poly(glutamic-co-leucine).

15. Device according to claim 14, wherein said polyhydroxyacids comprise polycaprolactone, poly(L-lactide), poly(D-lactide), poly(L/D-lactide), poly(L/DL-lactide) polyglycolide, copolymers of lactide and glycolide, poly(DL-lactide-co-glycolide), poly(DL-lactide-co-caprolactone), copolymers of glycolide and trimethylene carbonate, poly(glycolide-co-trimethylene carbonate), polyhydroxybutyrate, polyhydroxyvalerate, copolymers of hydroxybutyrate and hydroxyvalerate.

16. Device according to claim 9, wherein the polymeric material has a degradation rate in vivo in the range of 6 weeks to 24 months.

17. Device according to claim 9, wherein the polymeric material has a at least partially oriented structure.

18. Device according to claim 1, wherein said polymeric material has a polydispersity in the range of 1.2 to 100.0.

19. Device according to claim 18, wherein said polymeric material has a polydispersity in the range of 1.5 to 3.0.

20. Device according to claim 1 wherein said head is designed a grip portion for releasable engagement by a hollow introducer, said grip portion being preferably provided with a predetermine breaking or cutting point.

21. Device according to claim 1, wherein orientation of said retention elements in the upper shaft portion adjacent to said head is reversed in the opposite direction adjacent to the tip.

* * * * *